United States Patent
Wey (10) Patent No.: US 12,343,561 B2
(45) Date of Patent: Jul. 1, 2025

(54) CERAMIC MODULE EMITTING FAR INFRARED RADIATION AND SPECIFIC LOW DOSE IONIZING RADIATION

(71) Applicant: Albert Chin-Tang Wey, Westmont, IL (US)

(72) Inventor: Albert Chin-Tang Wey, Westmont, IL (US)

( * ) Notice: Subject to any disclaimer, the term of this patent is extended or adjusted under 35 U.S.C. 154(b) by 1263 days.

(21) Appl. No.: 16/943,973

(22) Filed: Jul. 30, 2020

(65) Prior Publication Data

US 2022/0032086 A1    Feb. 3, 2022

(51) Int. Cl.
| | | |
|---|---|---|
| *A61N 5/10* | (2006.01) | |
| *A61K 51/02* | (2006.01) | |
| *A61K 51/12* | (2006.01) | |
| *A61N 5/06* | (2006.01) | |
| *C09K 11/02* | (2006.01) | |
| *C09K 11/63* | (2006.01) | |

(52) U.S. Cl.
CPC ............ *A61N 5/1028* (2013.01); *A61K 51/02* (2013.01); *A61K 51/1241* (2013.01); *A61N 5/0613* (2013.01); *C09K 11/02* (2013.01); *C09K 11/636* (2013.01); *A61N 2005/0632* (2013.01); *A61N 2005/0645* (2013.01); *A61N 2005/066* (2013.01); *A61N 2005/1019* (2013.01)

(58) Field of Classification Search
CPC ................ A61N 5/1028; A61N 5/1029; A61N 2005/0632; A61N 2005/0645; A61N 2005/066; A61N 2005/1019; A61K 51/02; A61K 51/1241; C09K 11/02; C09K 11/636

See application file for complete search history.

(56) References Cited

U.S. PATENT DOCUMENTS

| | | |
|---|---|---|
| 6,200,537 B1 | 3/2001 | Watanabe et al. |
| 6,402,991 B1 | 6/2002 | Itakura et al. |
| 6,890,457 B2 | 5/2005 | Umehara et al. |
| 7,395,554 B2 | 7/2008 | Kitayama |
| 7,406,956 B1 | 8/2008 | Fujii |

(Continued)

FOREIGN PATENT DOCUMENTS

| | | | | |
|---|---|---|---|---|
| CN | 107812318 | * | 3/2018 | ............ A61H 39/00 |
| CN | 111374884 A | | 7/2020 | |

(Continued)

OTHER PUBLICATIONS

European Patent Office, "European Search Report" issued Dec. 22, 2021 in European patent application No. EP21182356.2.

*Primary Examiner* — Carrie R Dorna
(74) *Attorney, Agent, or Firm* — IpHorgan Ltd.

(57) ABSTRACT

This invention relates to a ceramic module for assembly into a therapeutic device for treating a human or animal body with irradiation of far infrared radiation and low dose ionizing radiation based on radiation hormesis effect. More specifically, the invention relates to a ceramic module that simultaneously emits far infrared radiation within 3-16 μm wavelength spectrum and ionizing radiation at a specific dose rate in the range of 0.1-11 μSv/h (micro-Sieverts per hour). Said ceramic module may be used alone or serve as components of a therapeutic device for increasing physiologic performance, immune competence, health, and mean lifespan of human or animal.

12 Claims, 3 Drawing Sheets

(56) References Cited

U.S. PATENT DOCUMENTS

| | | |
|---|---|---|
| 7,637,858 B2 | 12/2009 | Miyasaka |
| 7,976,934 B2 | 7/2011 | Arai |
| 8,104,455 B2 | 1/2012 | Kitajima et al. |
| 8,176,899 B2 | 5/2012 | Lee |
| 9,833,509 B2 * | 12/2017 | Vissman ................ A61K 33/22 |
| 10,610,699 B2 | 4/2020 | Wey |
| 2005/0075530 A1 * | 4/2005 | Kaizuka .................. A61N 5/06 |
| | | 600/9 |
| 2012/0175526 A1 | 7/2012 | Seo et al. |
| 2017/0312539 A1 * | 11/2017 | Wey ........................ A61N 5/06 |

FOREIGN PATENT DOCUMENTS

| | | | | |
|---|---|---|---|---|
| CS | 213314 | * | 4/1982 | ........... C03C 13/002 |
| JP | H10192426 A | | 7/1998 | |
| KR | 100419478 | * | 2/2004 | ............. A41B 11/00 |
| WO | 2018096651 A1 | | 5/2018 | |

* cited by examiner

CERAMIC MODULE EMITTING FAR INFRARED RADIATION AND SPECIFIC LOW DOSE IONIZING RADIATION

BACKGROUND

Field of Invention

This invention relates to a ceramic module for assembly into a therapeutic device for treating a human or animal body with irradiation of far infrared radiation and low dose ionizing radiation based on radiation hormesis effect. More specifically, the invention relates to a ceramic module that simultaneously emits far infrared radiation within 3-16 μm wavelength spectrum and ionizing radiation at a specific dose rate in the range of 0.1-11 μSv/h (micro-Sieverts per hour). Said ceramic module may be used alone or serve as components of a therapeutic device for increasing physiologic performance, immune competence, health, and mean lifespan of human or animal.

Description of Prior Art

Hormesis is the stimulation of any system by low doses of any agent. Radiation hormesis is the hypothesis that ionizing radiation is benign at low levels of exposure and can be beneficial. This is in contrast to the Linear-No-Threshold (LNT) model which posits that the negative health effects of ionizing radiation are proportional to the dose and there is no "safe dose" (threshold).

While most authorities agree that the LNT model is most appropriate, numerous studies have proposed radiobiological hormesis, suggesting that radiation levels of 100 mSv/y (milli-Sieverts per year) may actually be positive or at least neutral to health.

The effect of ionizing radiation on human body can be described as follows. The initial action of ionizing radiation is on the water ($H_2O$) which constitutes about 98% of the total number of molecules in soft tissues. Ionizing radiation produces a variety of oxygen species from water, including ions/radicals such as $H_3O^+$ (hydronium ion), $H_2O^+$ (oxonium ion), $HO^+$ (hydroxonium ion), $HO^-$ (hydroxyl radical), $HO_2^-$ (perhydroxyl radical), $O^-$ (oxygen radical), $O_2^-$ (superoxide ion), $O_2^{2-}$ (peroxide ion), $O_3^-$ (ozonide ion), and $HO_2^-$ (perhydroxide ion). Each of these ions/radicals will avidly attack nearby material to make strange compounds and atomic fragments (free radicals), resulting in change of the structure of DNA and RNA, which will drastically alter metabolic pathways and kill tissue cells.

This has the potential to cause harmful effects to people, especially at high levels of exposure. Thus, it becomes a common knowledge that ionizing radiation can penetrate the human body and the radiation energy can be absorbed in tissue; Ionizing activity can alter molecules within the cells of our body; Intense exposures to ionizing radiation may produce skin or tissue damage, which may cause eventual harm (such as cancer); and so forth.

Nonetheless, scientific studies have demonstrated that low dose irradiation is insufficient to kill healthy mammalian cells. If the rate of destruction is not too fast, damage in healthy tissues can be bypassed or repaired and the overall reaction may be "bio-positive". A major effect is activation of the immune system.

Low dose irradiation activates the immune system in several ways: faster wound healing, and increased resistance to toxins, infections, and tumor cell injections. For example, scientific research has demonstrated that lymphocyte production was increased by low dose irradiation. The search and destroy function of lymphocytes is facilitated by destruction of the radiation sensitive T repressor cells; this allows other T cells to be more efficient.

Other research paper also shows that cell concentrations of many important components of the immune system (enzymes and metabolites) are increased by low dose irradiation of the host. Changes in cell functions and enzyme characteristics support the radiation hormesis thesis. Evidently, increased immune competence contributes to increased mean lifespan in lightly irradiated laboratory animals and humans.

When compared with non-irradiated controls, cohorts exposed to low dose irradiation show statistically significant increased physiologic functions. Low dose irradiation stimulates many physiologic parameters that are consistent with damage control and improved health. For example, low dose irradiation of the torso was the most effective treatment for malignant lymphoma and decreased cancer death rates. Experimental data shows that in 40% of animal experiments there is a decrease in the incident of spontaneous cancer after low dose irradiation.

Radiation hormesis theory suggests that a beneficial dose-response effect may exist in a range of low-dose levels delineated by the background radiation dose rate (1 mSv/y) and a safety maximum dose limit (100 mSv/y). At any given rate, the physiologic response to ionizing radiation is directly proportional to the logarithm of the dose. It means that a beneficial response may be manipulated and realized with irradiation dose rates in the range of 1-100 mSv/y, but only if such a radiation source exists.

The present inventor further identifies a subdivision at exposure levels of 1-20 mSv/y that presents a safe dose for optimal biological effect. The best performance dose rate is equivalent to 0.1-2.3 μSv/h (for 1 year=8,760 hours).

The present inventor has also studied that, if there is only partial body irradiation, the calculation of effective dose must take account of the individual organ doses received, because the sensitivity of each organ to irradiation depends on their tissue type. The tissue weighting factor is used to calculate those individual organ dose contributions. For examples, colon, lung, breast, and stomach have a tissue weighting factor ($W_T$) of 0.12, while bladder, liver, thyroid, and esophagus have a $W_T$ of 0.04. The skin and brain have the lowest $W_T$ of 0.01, and the remainder of body has 0.12. This summed dose from only those organs considered gives the effective dose for the whole body.

Based on the study, the present inventor has recognized the need of dividing the theoretical scope of 1-100 mSv/y dose rate into portions and partitioning the radiation source into modules. An individual radiation module having a dose rate of 1-4 mSv/y (or approximately 0.1-0.5 μSv/h) would be desired. As such, a number of such modules may be assembled into a therapeutic device to emit any predetermined effective dose at discretion for practical applications.

During researching radiation hormesis theory, the present inventor has discovered that simultaneous supplementation with low dose ionizing irradiation and far infrared (FIR) radiation may have a strong interaction effect for more abundant health. Such radiation supplementation may manifest in the hydrolysis of Adenosine Triphosphate (ATP), as an example.

Hydrolysis is any chemical reaction in which a molecule of water ($H_2O$) breaks one or more chemical bonds. Biological hydrolysis is the cleavage of biomolecules (e.g. proteins, fats, oils, carbohydrates, and polysaccharides in the body) where a water molecule is consumed to prompt the separation of a larger molecule into component parts. The ionizing irradiation on water molecules produces a variety of oxygen ions/radicals from water, which may drastically improve the efficiency of water hydrolysis process.

ATP is a molecule that carries energy within cells. All living cells require a continual supply of energy for two main purposes: the biosynthesis of micro and macromolecules, and active transport of ions and molecules across cell membranes. In the human body, the energy derived from the oxidation of nutrients is not used directly, but it is channeled into a special energy-storage molecule, ATP.

When ATP is hydrolyzed, energy is released. ATP can undergo hydrolysis in two ways:

(where ADP=adenosine diphosphate; AMP=adenosine monophosphate;
$P_i$=phosphate; and $PP_i$=pyrophosphate).

The hydrolysis of ATP into ADP and inorganic phosphate ($P_i$) releases 30.5 kJ/mol of enthalpy, with a change in free energy of 3.4 kJ/mol.

The infrared absorption bands of ATP in above reaction are: P—O—P bond stretch at 9.75-11.48 μm and P=O bond stretch at 8.33-9.09 μm. Absorption of FIR photons may contribute about 11-15 KJ/mol to the reaction process, which may be significant.

Under the combined effects of FIR radiation and low dose ionizing radiation, hydrolysis of ATP can effectively provide energy to drive many processes in living cells, including muscle contraction, nerve impulse propagation, and chemical synthesis. With increased energy derived from ATP, cells can operate more efficiently, revitalize themselves, and repair damage.

ATP is one of four "monomers" required in the synthesis of RNA. The process is promoted by RNA polymerases. A similar process occurs in the formation of DNA, except that ATP is first converted to dATP (deoxyribonucleotide). DNA replication and DNA transcription also consumes ATP.

When the body has enough ATP, it is able to communicate effectively between organ systems, synthesize DNA and RNA, transporting chemicals into and out of cells, produce essential proteins, along with many other critical processes needed for cellular and organism survival. This eventually helps activate the immune system to offset the damage of DNA and RNA caused by low dose ionizing radiation.

In addition to being an essential energy source inside cells, ATP also carries critical message between cells, being used in signal transduction pathways for cell communication. For example, cells may be given signals to grow, metabolize, differentiate into specific types, or even die. ATP signaling may result in protective and healing response, including activating blood platelets for forming a clot to stop bleeding from a new wound. A similarly promising therapeutic area is the digestive system. ATP sent from intestinal nervous system to the intestinal wall acts on P2X and P2Y receptors to control the rhythmic contractions that move food through the tract. Thus, FIR, accompanied with low dose ionizing radiation, may be used as potential treatments for irritable bowel syndrome (IBS) and its more severe form, Crohn's disease.

ATP may also be one of the body's natural cancer-fighting tools. ATP signaling acts in part to promote apoptosis of the tumor cells and in part to promote cell differentiation, which slows tumor cell proliferation. Laboratory works have shown that ATP can inhibit the growth of tumors, including prostate, breast, colorectal, ovarian and esophageal cancers, and melanoma cells.

As disclosed above, simultaneous exposure to FIR radiation and low dose ionizing radiation may improve water hydrolysis efficiency and change the biochemical behavior of ATP molecules, offering unusual opportunities to improve human health. This new finding urges the need for a reliable and persistent radiation source that may simultaneously emit far infrared radiation and low dose ionizing radiation, as proposed in the present invention.

In summary, the present inventor finds that it would be desirable to have a ceramic module that can simultaneously emit far infrared radiation within 3-16 μm wavelength spectrum and ionizing radiation at a specific dose rate within 0.1-11 μSv/h. Said ceramic module may be used alone or for assembly into a therapeutic device that emits a maximal level of ionizing radiation not to exceed 11 μSv/h. Ionizing irradiation at a specific dose rate in 0.1-11 μSv/h (or 1-100 mSv/y) becomes a fundamental aspect of the present invention.

The prior art includes several inventions for improved fuel combustion efficiency which use far infrared emitting ceramic powders along with radioactive rare-earth mineral ore powders to generate so-called "negative ions" (e.g. U.S. Pat. Nos. 6,200,537, 7,406,956, 8,104,455, and 8,176,899). All these inventions fail to specify dose rate of ionizing radiation, which may present a latent risk of radiation overdosing in the proposed therapeutic applications when the device is brought to in close contact with the body for treatment.

For example, Fujii (U.S. Pat. No. 7,406,956) uses 15 g of radium that may irradiate at a dose rate up to 260 mSv/y, well above the allowed annual safety dose of 100 mSv/y. Lee (U.S. Pat. No. 8,176,899) uses an ore containing (Ce, Th, U)PO$_4$ from the monazite group that contains highly radioactive thorium-phosphate (ThPO$_4$). However, the thorium content of monazite varies considerably from mineral to mineral and from deposit to deposit. Monazite from certain carbonatites is essentially thorium-free, while in some other monazites the thorium content may be variable and sometimes can be up to 20-30%. The dose rate may potentially reach a hazardously high level >1 Sv/y.

Some inventions in prior art for therapeutic devices involve the use of FIR emitting ceramic powders along with "rare-earth elements" or "a powder of ore having natural radioactivity" (e.g. U.S. Pat. Nos. 6,402,991, 6,890,457, 7,395,554, 7,637,858, 7,976,934, and Pat Appl 20120175526). The radioactive substances used in these patents are mostly monazite and radium. Again, these inventions fail to specify radiation dose rate in the teachings and may most likely irradiate at a dose level that is unsuitable for hormesis effects. Besides, these inventions all use the substances in powder form, which is contradicting to the requirement for calcination of the powders mixture to form a shaped article, a ceramic module as proposed by the present invention, for assembly into a therapeutic device that may irradiate the body with a specific radiation dose rate at discretion, depending on the need for treatment.

Based on above discussion, the present inventor has discovered a new approach using a ceramic module that simultaneously emits far infrared radiation within 3-16 μm wavelength spectrum and ionizing radiation at a specific dose rate 0.1-11 μSv/h. Said ceramic module may be used alone or for assembly into a therapeutic device for increasing physiologic performance, immune competence, health, and mean lifespan of human or animal.

The prior art fails to teach the application of ionizing irradiation at a specific dose rate within 0.1-11 μSv/h for beneficial radiation hormesis effects. Furthermore, prior art's using radioactive substance but not specifying its radiation dose rate may cast the users a risk of overexposure to ionizing radiation greater than 11 μSv/h, which would be harmful and dangerous. Appropriate precautions should be taken by one who follows those teachings, especially to avoid direct contact with the devices of prior art.

Objects and Advantages

Accordingly, one object of this invention is to provide a ceramic module that simultaneously emits FIR radiation within 3-16 μm wavelength spectrum and ionizing radiation at a specific dose rate 0.1-11 μSv/h;

Another object of the present invention is to provide a ceramic module for assembly into a therapeutic device based on hormesis thesis to effectively improve the health conditions of human or animal body;

Also, another object of the present invention is to provide a simple, easy-to-use, and maintenance-free therapeutic device that is flexible to attach to any part of human or animal body that requires treatment.

These objectives are achieved by a ceramic module that simultaneously emits far infrared radiation within 3-16 μm wavelength spectrum and ionizing radiation at a specific dose rate <11 μSv/h. Said ceramic module comprises a shaped ceramic article made of essentially a mixture of powders of selected FIR-emitting oxides having specific spectral luminance covering at least a part of 3-16 μm wavelength spectrum and powders of radioactive oxides emitting ionizing radiation at a dose rate in 0.1-11 μSv/h. Said ceramic module may be secured in a flexible attachment means and placed at close proximity of the body part that requires treatment.

Other objects, features, and advantages of the present invention will hereinafter become apparent to those skilled in the art from the following description.

SUMMARY OF THE INVENTION

In accordance with the present invention a ceramic module comprises a mixture of powders of selected FIR-emitting oxides and powders of at least a radioactive element or oxide containing such radioactive element that emits ionizing radiation, said mixture being calcined along with bonding agents at a temperature above 900° C. into a shaped ceramic article to simultaneously emit far infrared radiation within 3-16 μm wavelength spectrum and ionizing radiation at a specific dose rate in 0.1-11 μSv/h that provides an effective means to improve health conditions of human or animal body based on radiation hormesis effects.

| Reference Numerals in Drawings | |
| --- | --- |
| 11 ceramic module | 21 substrate |
| 22 pockets | |

DETAILED DESCRIPTION OF THE INVENTION

The invention is a therapeutic device, comprising one or more ceramic modules of the present invention, the therapeutic device simultaneously emitting far infrared radiation within 3-16 μm wavelength spectrum and ionizing radiation at a specific dose rate in 0.1-11 μSv/h, wherein each said ceramic module is made of a mixture of one set of powders for emitting far infrared radiation and at least one set of powder for emitting low dose ionizing radiation. The mixture of powders is calcined with bonding agents and stabilizers at a temperature above 900° C. into a shaped article. In practical applications, each said ceramic module is designed to emit ionizing radiation at a dose rate in 0.1-0.5 μSv/h range so that an assembly of multiple ceramic modules may provide ionizing radiation at any specified dose rate in a fine scale within the range of 0.1-11 μSv/h for beneficial radiation hormesis effects.

The first set of powders for emitting FIR radiation may include one or more oxides selected from the group consisting of silicate, alumina, zirconia, phosphate, sodium oxide, potassium oxide, ferric oxide, chromic oxide, titanium oxide, magnesium oxide, manganese oxide, calcium oxide, nickel oxide, and cobalt oxide, that have a specific spectral luminance covering at least a part of the 3-16 μm wavelength spectrum. "Specific spectral luminance" is a term of art in the field of engineered ceramics. The term refers to the band of wavelengths of photons emitted by a FIR-emitting ceramic, in which 90% of the total energy is emitted.

The second set of powders for emitting ionizing radiation comprises one or more radioactive isotopes of elements, or oxides containing such isotopes, specifically including at least one of uranium, thorium, potassium, cobalt, and radium. Said powders may be processed from synthesized rare-earth oxides or natural minerals containing such radioactive isotopes of elements.

It is worthwhile to point out that the invention is not concerned with the content of "rare-earth" elements in natural minerals, but rather the naturally occurring radioactive isotopes contained within the minerals. Also, the radiation of "negative ions" or "minus ions" from the minerals as disclosed in prior art is irrelevant to radiation hormesis theory. Instead, the ability of the therapeutic device to emit "ionizing radiation" from minerals at a specific dose rate within 0.1-11 μSv/h is an essential requirement of the present invention.

For example, the group labeled "monazite" actually includes three different minerals, MONAZITE-(La), MONAZITE-(Nd), and MONAZITE-(Ce). Although all three minerals may contain variable percentage of rare-earth elements (La, Nd, Ce) in the mineral, MONAZITE-(La), MONAZITE-(Nd) are essentially thorium-free, while in MONAZITE-(Ce) the thorium content may be variable and sometimes can be up to 20-30%. Uranium is also a trace element in some specimens that makes them radioactive, but barely. All three monazite minerals may emit "negative ions (or "minus ions") as taught by prior art, only MONAZITE-(Ce) with 6-12% thorium content is adequate for use in the present invention to provide the required dose of ionizing radiation.

It is very important to prepare radioactive powders only from those oxides or minerals with acknowledged radiation characteristics. Yet, it is an art to establish a correlation between the radiation dose rate of ensuing ceramic product and the weight % of radioactive component materials used in the overall mixture. It is empirical rather than theoretical. Based on the correspondence, a ceramic module for emitting ionizing radiation at any predetermined dose rate can be made by using the associated weight % of radioactive materials.

The mixture, along with bonding agents, catalysts, and stabilizers, is hard-pressed, followed by calcination process into a shaped article at a temperature above 900° C. During the process, calcination temperature plays a key role on the strength and stability of both consequential far infrared radiation and ionizing radiation of the resulting ceramic module.

Calcination processes include the decomposition of ores, hydrated minerals, and volatile matter, heat treatment to effect phase transformations, and removal of ions. Calcination reactions usually take place at or above the thermal decomposition temperature (for decomposition and volatilization reactions) or the transition temperature (for phase transitions). This temperature is usually defined as the temperature at which the standard Gibbs free energy for a particular calcination reaction is equal to zero.

Following calcining, initial mineralogical differences between raw materials influence the textural and mineralogical evolution of the ceramics as temperature increases from 700 to 1200° C. Mineralogical and textural changes can be interpreted by considering local marked disequilibria in a system that resembles a small-scale high-temperature metamorphic process.

Infrared radiation spectrum and spectral strength depend on several factors, including mixture of oxides, calcining temperature, and the polycrystalline structure of the resulting ceramic composite. The composite has a mixture of crystalline and amorphous regions. Each crystalline region works as a dipole that has an electric dipole moment due to molecular asymmetry, which determines the chemical properties of the system, such as dipole moment and allowed spectroscopic transitions, based on Selection Rule (Laporte rule).

In the ceramic module of the present invention, heat transfer arises from temperature gradients (i.e. temperature differences caused by absorption of ambient heat radiation) through the diffuse exchange of microscopic kinetic and potential particle energy, resulting in dipole oscillation that produces electromagnetic radiation. A photon is released at a frequency v depending on the change in dipole potential; $\Delta U_{dipole} = h\nu$, where h is Planck constant. The formula can be further reduced to be: $E (eV) = 1.2398/\lambda (\mu m)$; where $\lambda (\mu m)$ is wavelength of FIR photon.

A controlled calcination process that follows hard-pressing of the mixture of powders helps bring grains together. It increases compaction ratio of crystal system, with increases density, reduces surface area, and decreases free energy of the system. In addition, it increases contact area between grains by removing pores and thus enhances ions diffusion and dispersion at grain boundary. Ions such as $Al^{3+}$, $Ca^{2+}$, $K^+$, $Fe^{2+}$, $Mg^{2+}$, $O^{2-}$, and $H^+$ can freely relocate in the crystal system for re-crystallization and directional grain growth that results in phase transformation in crystal structure.

To give an example, zirconia ($ZrO_2$) may be stabilized with phase transformation from monoclinic to tetragonal by calcining at 1170° C. Also, tourmaline may lose its pyro-electricity at a temperature above 950° C. through phase transformation.

Controlled calcination at a temperature above 1100° C. may help align individual dipoles to result in coherent dipole moments of the system. It can be envisioned as small increments of quasi-static adiabatic work in terms of statistical distribution of an ensemble of microstates.

Additionally, using the MONAZITE-(Ce) system as an example, the crystal structures of Ce, La, and Nd oxides transform from monoclinic to cubic with increasing calcination temperature above 1100° C. Calcination temperature may significantly affect the stability and radioactivity of ceramic module, regarding ionizing radiation.

That being said, a calcination temperature at or above 900° C. may turn the mixture of powders into a shaped ceramic module of the present invention, capable of emitting simultaneously far infrared radiation and ionizing radiation. Still, a calcination temperature above 1100° C. is preferred to make a reliable and persistent radiation source for FIR radiation in a desirable wavelength band and ionizing radiation at a specific dose rate.

Figure 1:
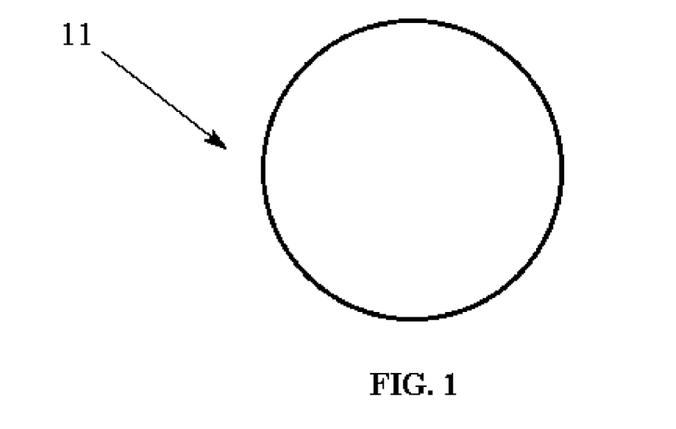
FIG. 1 is a perspective view of a first embodiment of the present invention showing a ceramic module in the shape of a sphere.
Figure 2:
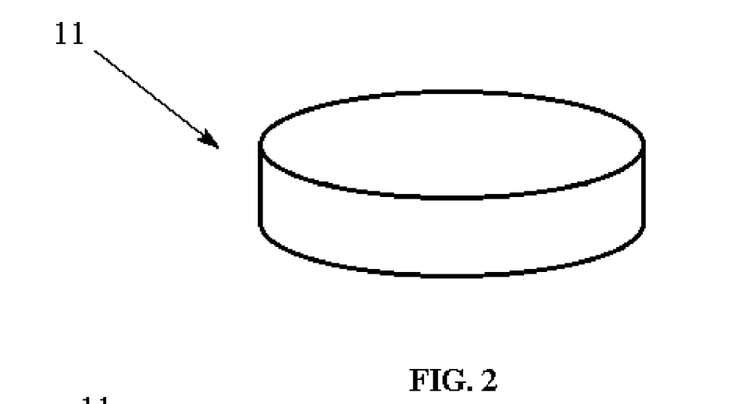
FIG. 2 is a perspective view of a second embodiment of the present invention showing a ceramic module in the shape of a circular plate.
Figure 3:
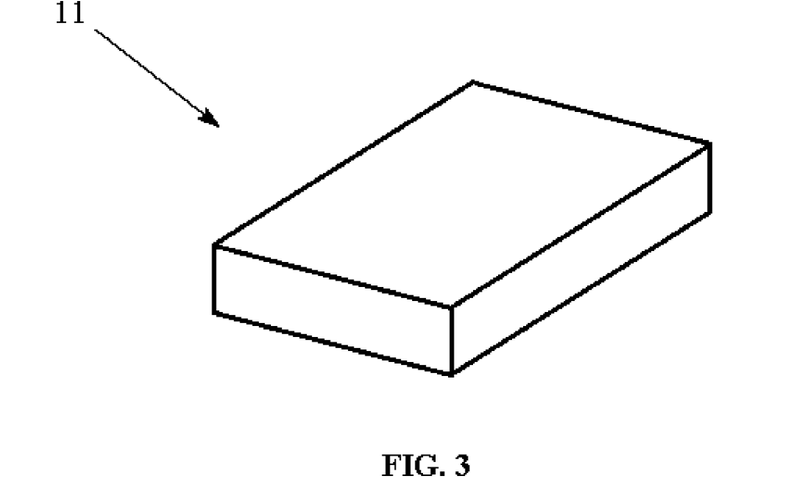
FIG. 3 is a perspective view of a third embodiment of the present invention showing a ceramic module in the shape of a rectangular plate.

FIGS. 1-3 show three separate embodiments of the present invention of varying shapes: in FIG. 1, the ceramic module 11 is shaped as a sphere, in FIG. 2, the ceramic module 11 is shaped as a circular plate, and in FIG. 3, the ceramic module 11 is shaped as a rectangular plate.

The ceramic module(s) 11 of the present invention may be formed into various shapes and sizes, depending upon applications. In at least one embodiment, the IR-emitting elements may be circular in shape, and may be a 2-50 mm diameter circle with a thickness of 1-10 mm. In another embodiment, the IR-emitting elements may be rectangular, having dimensions of a 2 by 3 mm rectangle to a 40 by 50 mm rectangle, with a thickness of 1-10 mm. Rectangular and circular shaped ceramics are generally easier to fabricate than other shapes.

Figure 4:
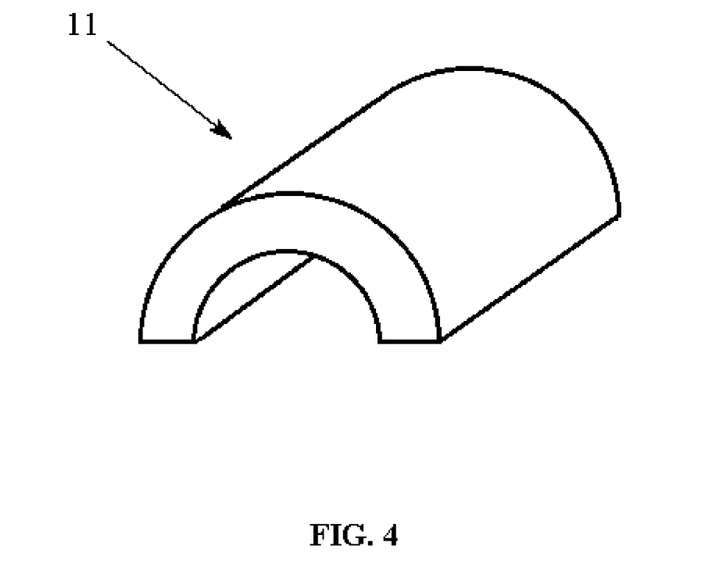
FIG. 4 is a perspective view of a fourth embodiment of the present invention showing a ceramic module in the shape of a partial cylinder.

Nonetheless, it may be advantageous to form the ceramic module 11 with a concave shape. As it can be appreciated, each ceramic module 11 emits FIR radiation and ionizing radiation in all directions. It is anticipated that a concave surface will help focus the rays of radiation emitted by the ceramic module in a region or point at a distance from the surface of the therapeutic device. The focused radiation would penetrate the body with less attenuation than unfocused rays from a ceramic with a flat surface, and would thereby provide an increased therapeutic effect compared to flat ceramics of similar mass and dimensions. The concave surface may take a variety of shapes, such as hemispherical, bowl-shaped, or a partial cylinder. FIG. 4 shows an embodiment of the present invention, in which ceramic module 11 has a partial cylinder shape.

Figure 5:
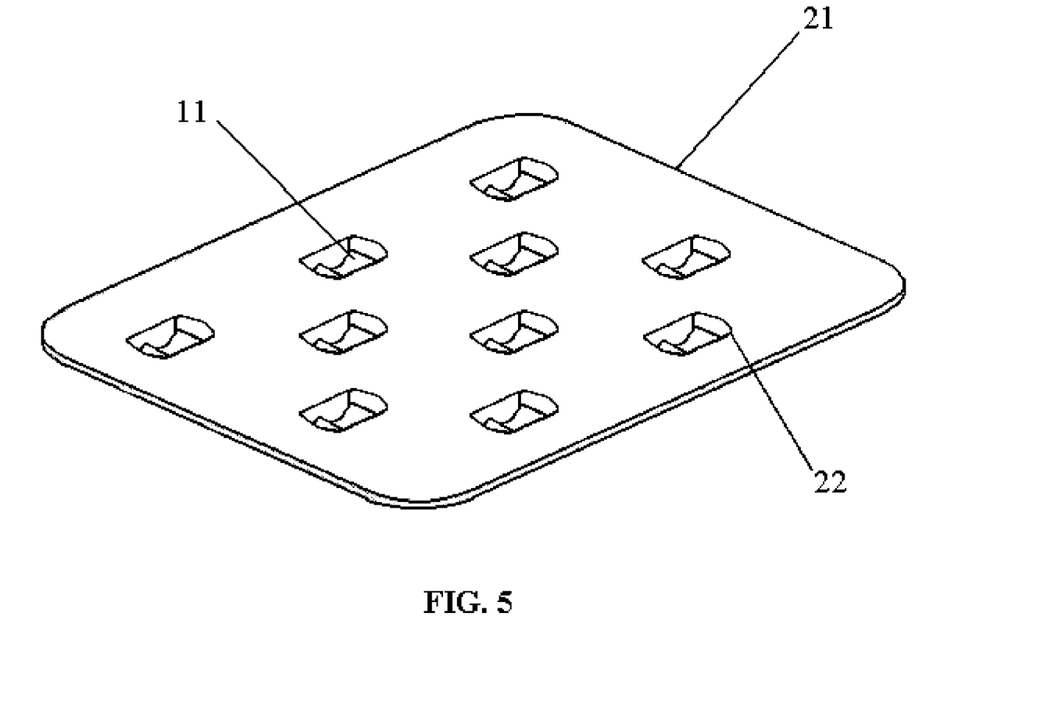
FIG. 5 is a top perspective view of a fifth embodiment of the present invention showing multiple ceramic modules are mounted on a flexible substrate for attaching to a body part to be treated, wherein each of ceramic module has a concave surface facing the body.
Figure 6:
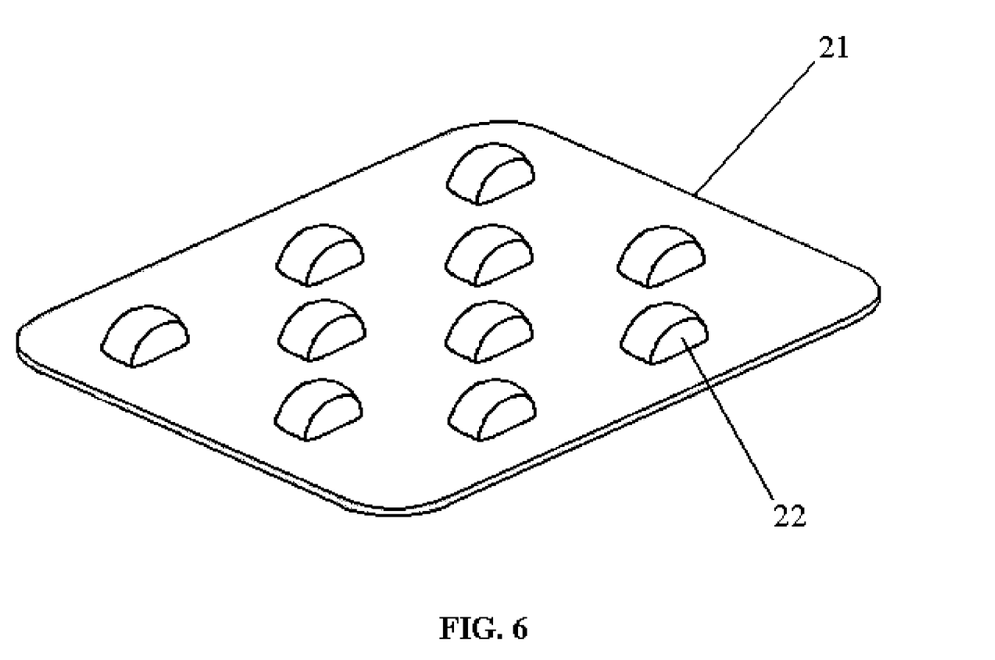
FIG. 6 is a bottom perspective view of the embodiment of FIG. 5, showing the pockets containing the concave ceramic modules.

FIG. 5 shows a preferred embodiment of the present invention, in which multiple ceramic modules 11 are embedded in a substrate 21, which may be made from silicone (polydimethylsiloxane), zinc sulfide, sodium chloride, potassium bromide, or similar materials. The substrate 21 is a substantially flat sheet that includes a number of pockets 22, which are curved protrusions dimensioned to contain ceramic modules 11. FIG. 6 illustrates the underside of substrate 21, which faces away from the body part being treated. In this embodiment, all pockets 22 have the same dimension because all ceramic modules 11 have the same dimensions. In other embodiments, however, pockets 22 may have different sizes or shapes tailored to specific applications or arrangements of variable ceramic modules 11.

Also, the ceramic module 11 in FIG. 5 has a partial cylindrical shape. The partial-cylindrical shaped ceramic module is arranged to have the concave surface facing toward the body part to be treated. This arrangement helps to focus FIR radiation at about one (1) inch above the surface of the device. When the device is wrapped closely around the body during use, the radiation will be focused to a depth of about one inch into the body tissue, and thus significantly enhance the radiation effect in the body.

The embodiments of the invention described thus far are passive devices. The ceramic module 11 absorbs ambient radiation heat and convert the heat into FIR photons. FIR radiation from the ceramic module 11 will last indefinitely, wherever the ambient temperature is greater than Absolute Zero (i.e. 0 deg. K or −273 deg. C.). Obviously, body heat is a natural heat source for ceramic module 11 to emit far infrared radiation.

On the other hand, ionizing radiation from ceramic module 11 lasts for a very long time, because it is formed from naturally occurring radioactive isotopes which, by necessity, have extremely long lifetimes. The radioactivity of an isotope is strongly dependent upon its half-life. For examples, Uranium-239 has a half-life of 4.5 billion years and Thorium-232 is with a half-life of 14 billion years that have lasted as long as the Earth.

The ceramic module of present invention can be fabricated by the following process. First, prepare a mixture of powders of oxides containing, by weight, 24% $SiO_2$, 16% $Al_2O_3$, 15% $Fe_2O_3$, 13% $ZrO_3$, 4% CoO, 3% BaO, 3% $K_2O$, 3% $Cr_2O_3$, 0.5% MgO, 0.5% $Na_2O$, 15% tourmaline, 2% Thorite, and other minority oxides. The mixture of powders, along with bonding agents, catalysts, and stabilizers, is press-molded to the desired shapes and calcined in a furnace at a temperature of 1200° C. Accordingly, several samples were prepared for concept-demonstrating lab experiments and clinical trials.

In experiments, the ceramic modules are made into a shape of ⅓-circumference cutout of a 12-mm long cylindrical tube, with 15-mm I.D. (inner diameter) and 30-mm O.D. (outer diameter). The specific spectral luminance of the ceramic module was measured to cover the 3-16 μm wavelength spectrum, while the ionizing radiation dose rate was detected to be 0.15-0.25 μSv/h (micro-Sievert per hour).

All experimental samples were arranged in an array formation as shown in FIG. 5 and secured with polysulfide rubber mold compound. The concave side is arranged to face toward the body to be treated. A penetration depth of about 1 inch into the body is anticipated. The FIR photons and ionizing radiation absorbed by the body are believed to be carried around through the body by blood circulation for beneficial health effects, based on radiation hormesis.

Encouraging results with the device of present invention have been observed in lab animal experiments and clinical trials, with respect to wounds healing, repair and growth of previously damaged cells, and proliferation of stem cells, compared to controls.

CONCLUSION, RAMIFICATIONS, AND SCOPE

According to the present invention, a ceramic module for treating a human or animal body, based on radiation hormesis thesis, can simultaneously emit far infrared radiation within 3-16 μm wavelength spectrum and ionizing radiation at a specific dose rate in 0.1-11 μSv/h (micro-Sievert per hour). Said ceramic module may be used alone or serve as components of a therapeutic device for increasing physiologic performance, immune competence, health, and mean lifespan of human or animal.

The invention has been described above. Obviously, numerous modifications and variations of the present invention are possible in light of the above teachings. Such variations are not to be regarded as a departure from the spirit and scope of the invention and all such modifications as would be obvious to one skilled in the art are intended to be included within the scope of the following claims.

I claim:

1. A ceramic module for use in a therapeutic device for treating a human or animal body, said ceramic module comprising a mixture of a first set of powdered substance emitting far infrared radiation and a second set of powdered substance emitting ionizing radiation, wherein as a result of the mixture of the first and second sets of powdered substances being calcined at a temperature at or above 900° C. into a shaped article comprising at least one dipole crystalline region and at least one amorphous region, said ceramic module simultaneously emits far infrared radiation within 3-16 μm wavelength spectrum and ionizing radiation at a specific dose rate in the range of 0.1-11 μSv/h.

2. The ceramic module according to claim 1, wherein the ionizing radiation dose rate of said ceramic module is in the range of 0.1-0.5 μSv/h.

3. The ceramic module according to claim 1, wherein said first set of powdered substance includes one or more oxides selected from the group consisting of silicate, alumina, zirconia, phosphate, sodium oxide, potassium oxide, ferric oxide, chromic oxide, titanium oxide, magnesium oxide, manganese oxide, calcium oxide, nickel oxide, and cobalt oxide, wherein at least one of the selected oxides is at least 2% by weight of the first set of powdered substance.

4. The ceramic module according to claim 1, wherein said first set of powdered substance includes approximately 5-30% by weight of tourmaline.

5. The ceramic module according to claim 1, wherein said second set of powdered substance includes at least one radioactive isotope of uranium, thorium, potassium, cobalt, or radium.

6. The ceramic module according to claim 1, wherein said second set of powdered substance includes at least one oxide containing a radioactive isotope of uranium, thorium, potassium, cobalt, or radium.

7. The ceramic module according to claim 1, wherein said second set of powdered substance includes at least one mineral containing a radioactive isotope of uranium, thorium, potassium, cobalt, or radium.

8. The ceramic module according to claim 7, wherein the at least one mineral is thorite or uraninite.

9. The ceramic module according to claim 7, wherein the at least one mineral is thorium-rich monazite.

10. The ceramic module according to claim 9, wherein said thorium-rich monazite contains 6-12% thorium oxide.

11. The ceramic module according to claim 1, wherein said ceramic module is rectangular, circular, cylindrical, or spherical in shape.

12. The ceramic module according to claim 1, wherein said ceramic module is mounted on a flexible substrate for attaching to a body part to be treated.

* * * * *